(12) United States Patent
Diaz et al.

(10) Patent No.: US 9,254,202 B2
(45) Date of Patent: Feb. 9, 2016

(54) METHOD AND APPARATUS FOR LOADING A BENEFICIAL AGENT INTO AN EXPANDABLE MEDICAL DEVICE

(71) Applicant: Innovational Holdings LLC, New Brunswick, NJ (US)

(72) Inventors: Stephen Hunter Diaz, Palo Alto, CA (US); Kinam Park, West Lafayette, IN (US)

(73) Assignee: Innovational Holdings LLC, Irvine, CA (US)

( * ) Notice: Subject to any disclaimer, the term of this patent is extended or adjusted under 35 U.S.C. 154(b) by 89 days.

(21) Appl. No.: 13/736,752

(22) Filed: Jan. 8, 2013

(65) Prior Publication Data

US 2013/0127089 A1 May 23, 2013

Related U.S. Application Data

(60) Continuation-in-part of application No. 12/841,903, filed on Jul. 22, 2010, now Pat. No. 8,349,390, which is a division of application No. 10/447,587, filed on May 28, 2003, now abandoned.

(60) Provisional application No. 60/412,489, filed on Sep. 20, 2002.

(51) Int. Cl.
*A61F 2/82* (2013.01)
*A61F 2/91* (2013.01)
(Continued)

(52) U.S. Cl.
CPC ... *A61F 2/82* (2013.01); *A61F 2/91* (2013.01); *A61F 2/915* (2013.01); *A61L 31/146* (2013.01);
(Continued)

(58) Field of Classification Search
CPC .............. A61F 2/82; A61F 2250/0068; A61F 2240/001; A61F 2210/0076; A61F 2/00; B05D 1/00
USPC ......................................... 427/2.25; 623/1.15
See application file for complete search history.

(56) References Cited

U.S. PATENT DOCUMENTS 3,657,744 A 4/1972 Ersek
4,300,244 A 11/1981 Bokros
(Continued)

FOREIGN PATENT DOCUMENTS

CA 2234787 4/1998
DE 20200220 U1 1/2002
(Continued)

OTHER PUBLICATIONS

Lemos, Pedro A. et al., "Drug-Eluting Stents." Euro, May 2004.
(Continued)

*Primary Examiner* — Vy Bui
(74) *Attorney, Agent, or Firm* — Hamre, Schumann, Mueller & Larson, P.C.

(57) ABSTRACT

The present invention relates to method for loading a beneficial agent into an expandable medical device. The method includes the steps of sealing a plurality of openings extending through the medical device from a first side to a second side with a sealing member to substantially prevent a beneficial agent from passing through the openings, partially filling the openings with the beneficial agent delivered from an automated micro-jetting dispenser, substantially solidifying the beneficial agent, and removing the sealing member from the plurality of openings.

9 Claims, 3 Drawing Sheets

(51) Int. Cl.
*A61F 2/915* (2013.01)
*A61L 31/14* (2006.01)
*A61L 31/16* (2006.01)
*B01D 1/18* (2006.01)
*A61F 2/06* (2013.01)

(52) U.S. Cl.
CPC . *A61L 31/16* (2013.01); *B01D 1/18* (2013.01); *A61F 2002/061* (2013.01); *A61F 2002/821* (2013.01); *A61F 2002/91508* (2013.01); *A61F 2002/91516* (2013.01); *A61F 2002/91525* (2013.01); *A61F 2002/91533* (2013.01); *A61F 2002/91541* (2013.01); *A61F 2002/91558* (2013.01); *A61F 2250/0068* (2013.01); *A61L 2300/252* (2013.01); *A61L 2300/416* (2013.01)

(56) References Cited

U.S. PATENT DOCUMENTS

| | | |
|---|---|---|
| 4,531,936 A | 7/1985 | Gordon |
| 4,542,025 A | 9/1985 | Tice et al. |
| 4,580,568 A | 4/1986 | Gianturco |
| 4,650,466 A | 3/1987 | Luther |
| 4,733,665 A | 3/1988 | Palmaz |
| 4,739,762 A | 4/1988 | Palmaz |
| 4,776,337 A | 10/1988 | Palmaz |
| 4,800,882 A | 1/1989 | Gianturco |
| 4,824,436 A | 4/1989 | Wolinsky |
| 4,834,755 A | 5/1989 | Silvestrini et al. |
| 4,955,878 A | 9/1990 | See et al. |
| 4,957,508 A | 9/1990 | Kaneko et al. |
| 4,960,790 A | 10/1990 | Stella et al. |
| 4,969,458 A | 11/1990 | Wiktor |
| 4,989,601 A | 2/1991 | Marchosky |
| 4,990,155 A | 2/1991 | Wilkoff |
| 4,994,071 A | 2/1991 | MacGregor |
| 5,019,090 A | 5/1991 | Pinchuk |
| 5,049,132 A | 9/1991 | Shaffer et al. |
| 5,053,048 A | 10/1991 | Pinchuk |
| 5,059,166 A | 10/1991 | Fischell et al. |
| 5,059,211 A | 10/1991 | Stack et al. |
| 5,078,726 A | 1/1992 | Kreamer |
| 5,092,841 A | 3/1992 | Spears |
| 5,102,417 A | 4/1992 | Palmaz |
| 5,157,049 A | 10/1992 | Haugwitz et al. |
| 5,171,217 A | 12/1992 | March et al. |
| 5,171,262 A | 12/1992 | MacGregor |
| 5,176,617 A | 1/1993 | Fischell et al. |
| 5,195,984 A | 3/1993 | Schatz |
| 5,197,978 A | 3/1993 | Hess |
| 5,213,580 A | 5/1993 | Slepian et al. |
| 5,234,456 A | 8/1993 | Silvestrini |
| 5,242,399 A | 9/1993 | Lau et al. |
| 5,286,254 A | 2/1994 | Shapland et al. |
| 5,292,512 A | 3/1994 | Schaefer et al. |
| 5,304,121 A | 4/1994 | Sahatjian |
| 5,314,688 A | 5/1994 | Kauffman et al. |
| 5,342,348 A | 8/1994 | Kaplan |
| 5,342,621 A | 8/1994 | Eury |
| 5,344,426 A | 9/1994 | Lau et al. |
| 5,380,299 A | 1/1995 | Fearnot et al. |
| 5,383,892 A | 1/1995 | Cardon et al. |
| 5,383,928 A | 1/1995 | Scott et al. |
| 5,403,858 A | 4/1995 | Bastard et al. |
| 5,407,683 A | 4/1995 | Shively |
| 5,415,869 A | 5/1995 | Straubinger et al. |
| 5,419,760 A | 5/1995 | Narciso, Jr. |
| 5,439,446 A | 8/1995 | Barry |
| 5,439,686 A | 8/1995 | Desai et al. |
| 5,441,515 A | 8/1995 | Khosravi et al. |
| 5,441,745 A | 8/1995 | Presant et al. |
| 5,443,496 A | 8/1995 | Schwartz et al. |
| 5,443,497 A | 8/1995 | Venbrux |
| 5,443,500 A | 8/1995 | Sigwart |
| 5,447,724 A | 9/1995 | Helmus et al. |
| 5,449,373 A | 9/1995 | Pinchasik et al. |
| 5,449,513 A | 9/1995 | Yokoyama et al. |
| 5,457,113 A | 10/1995 | Cullinan et al. |
| 5,460,817 A | 10/1995 | Langley et al. |
| 5,462,866 A | 10/1995 | Wang |
| 5,464,450 A | 11/1995 | Buscemi et al. |
| 5,464,650 A | 11/1995 | Berg et al. |
| 5,473,055 A | 12/1995 | Mongelli et al. |
| 5,523,092 A | 6/1996 | Hanson et al. |
| 5,545,210 A | 8/1996 | Hess et al. |
| 5,551,954 A | 9/1996 | Buscemi et al. |
| 5,556,413 A | 9/1996 | Lam |
| 5,575,771 A | 11/1996 | Walinsky |
| 5,578,075 A | 11/1996 | Dayton |
| 5,593,434 A | 1/1997 | Williams |
| 5,607,442 A | 3/1997 | Fischell et al. |
| 5,609,629 A | 3/1997 | Fearnot et al. |
| 5,616,608 A | 4/1997 | Kinsella et al. |
| 5,617,878 A | 4/1997 | Taheri |
| 5,618,299 A | 4/1997 | Khosravi et al. |
| 5,624,411 A | 4/1997 | Tuch |
| 5,628,787 A | 5/1997 | Mayer |
| 5,643,314 A | 7/1997 | Carpenter et al. |
| 5,667,764 A | 9/1997 | Kopia et al. |
| 5,674,278 A | 10/1997 | Boneau |
| 5,697,971 A | 12/1997 | Fischell et al. |
| 5,707,385 A | 1/1998 | Williams |
| 5,713,949 A | 2/1998 | Jayaraman |
| 5,716,981 A | 2/1998 | Hunter et al. |
| 5,725,548 A | 3/1998 | Jayaraman |
| 5,725,549 A | 3/1998 | Lam |
| 5,733,330 A | 3/1998 | Cox |
| 5,733,925 A | 3/1998 | Kunz et al. |
| 5,741,293 A | 4/1998 | Wijay |
| 5,759,192 A | 6/1998 | Saunders |
| 5,766,239 A | 6/1998 | Cox |
| 5,769,883 A | 6/1998 | Buscemi et al. |
| 5,776,181 A | 7/1998 | Lee et al. |
| 5,780,807 A | 7/1998 | Saunders |
| 5,797,898 A | 8/1998 | Santini, Jr. |
| 5,800,507 A | 9/1998 | Schwartz |
| 5,807,404 A | 9/1998 | Richter |
| 5,817,152 A | 10/1998 | Birdsall et al. |
| 5,824,045 A | 10/1998 | Alt |
| 5,824,049 A | 10/1998 | Ragheb et al. |
| 5,827,322 A | 10/1998 | Williams |
| 5,836,964 A | 11/1998 | Richter et al. |
| 5,837,313 A | 11/1998 | Ding et al. |
| 5,843,117 A | 12/1998 | Alt et al. |
| 5,843,120 A | 12/1998 | Israel et al. |
| 5,843,172 A | 12/1998 | Yan |
| 5,843,175 A | 12/1998 | Frantzen |
| 5,843,741 A | 12/1998 | Wong et al. |
| 5,853,419 A | 12/1998 | Imran |
| 5,855,600 A | 1/1999 | Alt |
| 5,868,781 A | 2/1999 | Killion |
| 5,873,904 A | 2/1999 | Ragheb et al. |
| 5,876,419 A | 3/1999 | Carpenter et al. |
| 5,882,335 A | 3/1999 | Leone et al. |
| 5,886,026 A | 3/1999 | Hunter et al. |
| 5,906,759 A | 5/1999 | Richter |
| 5,922,020 A | 7/1999 | Klein et al. |
| 5,922,021 A | 7/1999 | Jang |
| 5,957,971 A | 9/1999 | Schwartz |
| 5,964,798 A | 10/1999 | Imran |
| 5,968,092 A | 10/1999 | Buscemi et al. |
| 5,972,027 A | 10/1999 | Johnson |
| 5,972,180 A | 10/1999 | Chujo |
| 5,976,182 A | 11/1999 | Cox |
| 5,984,957 A | 11/1999 | Laptewicz, Jr. et al. |
| 5,992,000 A | 11/1999 | Humphrey et al. |
| 5,992,769 A | 11/1999 | Wise et al. |
| 5,994,341 A | 11/1999 | Hunter et al. |
| 5,997,703 A | 12/1999 | Richter |
| 6,007,517 A | 12/1999 | Anderson |
| 6,017,363 A | 1/2000 | Hojeibane |
| 6,019,789 A | 2/2000 | Dinh et al. |
| 6,022,371 A | 2/2000 | Killion |

(56) References Cited

U.S. PATENT DOCUMENTS

| | | | |
|---|---|---|---|
| 6,030,414 A | 2/2000 | Taheri | |
| 6,042,606 A | 3/2000 | Frantzen | |
| 6,056,722 A | 5/2000 | Jayaraman | |
| 6,063,101 A | 5/2000 | Jacobsen et al. | |
| 6,066,168 A | 5/2000 | Lau et al. | |
| 6,071,305 A | 6/2000 | Brown et al. | |
| 6,083,258 A | 7/2000 | Yadav | |
| 6,087,479 A | 7/2000 | Stamler et al. | |
| 6,096,070 A | 8/2000 | Ragheb et al. | |
| 6,099,561 A | 8/2000 | Alt | |
| 6,114,049 A | 9/2000 | Richter | |
| 6,120,535 A | 9/2000 | McDonald et al. | |
| 6,120,847 A | 9/2000 | Yang et al. | |
| 6,123,861 A | 9/2000 | Santini, Jr. et al. | |
| 6,131,266 A | 10/2000 | Saunders | |
| 6,153,252 A | 11/2000 | Hossainy et al. | |
| 6,156,062 A | 12/2000 | McGuinness | |
| 6,159,488 A | 12/2000 | Nagler et al. | |
| 6,174,326 B1 | 1/2001 | Kitaoka et al. | |
| 6,190,403 B1 | 2/2001 | Fischell et al. | |
| 6,193,746 B1 | 2/2001 | Strecker | |
| 6,197,048 B1 | 3/2001 | Richter | |
| 6,206,914 B1 | 3/2001 | Soykan et al. | |
| 6,206,915 B1 | 3/2001 | Fagan et al. | |
| 6,206,916 B1 | 3/2001 | Furst | |
| 6,231,600 B1 | 5/2001 | Zhong | |
| 6,240,616 B1 | 6/2001 | Yan | |
| 6,241,762 B1 | 6/2001 | Shanley | |
| 6,245,101 B1 | 6/2001 | Drasler et al. | |
| 6,249,952 B1 | 6/2001 | Ding | |
| 6,254,632 B1 | 7/2001 | Wu et al. | |
| 6,257,706 B1 | 7/2001 | Ahn | |
| 6,273,908 B1 | 8/2001 | Ndondo-Lay | |
| 6,273,910 B1 | 8/2001 | Limon | |
| 6,273,913 B1 | 8/2001 | Wright et al. | |
| 6,280,411 B1 | 8/2001 | Lennox | |
| 6,290,673 B1 | 9/2001 | Shanley | |
| 6,293,967 B1 | 9/2001 | Shanley | |
| 6,299,604 B1 | 10/2001 | Ragheb et al. | |
| 6,299,755 B1 | 10/2001 | Richter | |
| 6,306,166 B1 | 10/2001 | Barry et al. | |
| 6,309,414 B1 | 10/2001 | Rolando et al. | |
| 6,312,460 B2 | 11/2001 | Drasler et al. | |
| 6,331,189 B1 | 12/2001 | Wolinsky et al. | |
| 6,334,807 B1 | 1/2002 | Lebel et al. | |
| 6,334,871 B1 | 1/2002 | Dor et al. | |
| 6,369,355 B1 | 4/2002 | Saunders | |
| 6,375,826 B1 | 4/2002 | Wang et al. | |
| 6,378,988 B1 | 4/2002 | Taylor et al. | |
| 6,379,381 B1 | 4/2002 | Hossainy et al. | |
| 6,395,326 B1 | 5/2002 | Castro et al. | |
| 6,423,092 B2 | 7/2002 | Datta et al. | |
| 6,451,051 B2 | 9/2002 | Drasler et al. | |
| 6,475,237 B2 | 11/2002 | Drasler et al. | |
| 6,482,166 B1 | 11/2002 | Fariabi | |
| 6,491,666 B1 | 12/2002 | Santini, Jr. et al. | |
| 6,497,916 B1 | 12/2002 | Taylor et al. | |
| 6,506,411 B2 | 1/2003 | Hunter et al. | |
| 6,506,437 B1 | 1/2003 | Harish et al. | |
| 6,537,256 B2 | 3/2003 | Santini, Jr. et al. | |
| 6,544,544 B2 | 4/2003 | Hunter et al. | |
| 6,544,582 B1 | 4/2003 | Yoe | |
| 6,548,308 B2 | 4/2003 | Ellson et al. | |
| 6,554,838 B2 | 4/2003 | Santini et al. | |
| 6,558,733 B1 | 5/2003 | Hossainy et al. | |
| 6,562,065 B1 | 5/2003 | Shanley | |
| 6,565,602 B2 | 5/2003 | Rolando et al. | |
| 6,585,764 B2 | 7/2003 | Wright et al. | |
| 6,599,415 B1 | 7/2003 | Ku et al. | |
| 6,616,765 B1 * | 9/2003 | Castro et al. | 118/669 |
| 6,635,082 B1 | 10/2003 | Hossainy et al. | |
| 6,645,547 B1 | 11/2003 | Shekalim et al. | |
| 6,656,162 B2 | 12/2003 | Santini et al. | |
| 6,676,987 B2 | 1/2004 | Zhong et al. | |
| 6,679,980 B1 | 1/2004 | Andreacchi | |
| 6,682,771 B2 | 1/2004 | Zhong et al. | |
| 6,689,159 B2 | 2/2004 | Lau et al. | |
| 6,699,281 B2 | 3/2004 | Vallana et al. | |
| 6,723,373 B1 | 4/2004 | Narayanan et al. | |
| 6,730,064 B2 | 5/2004 | Ragheb et al. | |
| 6,730,116 B1 | 5/2004 | Wolinsky et al. | |
| 6,746,686 B2 | 6/2004 | Hughes et al. | |
| 6,752,829 B2 | 6/2004 | Kocur et al. | |
| 6,758,859 B1 * | 7/2004 | Dang et al. | 623/1.15 |
| 6,764,507 B2 | 7/2004 | Shanley et al. | |
| 6,774,278 B1 | 8/2004 | Ragheb et al. | |
| 6,776,796 B2 | 8/2004 | Falotico et al. | |
| 6,783,543 B2 | 8/2004 | Jang | |
| 6,783,793 B1 | 8/2004 | Hossainy et al. | |
| 6,790,228 B2 | 9/2004 | Hossainy et al. | |
| 6,805,898 B1 | 10/2004 | Wu et al. | |
| 6,808,536 B2 | 10/2004 | Wright et al. | |
| 6,818,063 B1 | 11/2004 | Kerrigan | |
| 6,827,966 B2 * | 12/2004 | Qiu et al. | 427/2.24 |
| 6,849,089 B2 | 2/2005 | Stoll | |
| 6,852,123 B2 | 2/2005 | Brown | |
| 6,855,125 B2 | 2/2005 | Shanley | |
| 6,860,946 B2 | 3/2005 | Hossainy et al. | |
| 6,861,088 B2 | 3/2005 | Weber et al. | |
| 6,863,685 B2 | 3/2005 | Davila et al. | |
| 6,865,810 B2 | 3/2005 | Stinson | |
| 6,866,810 B2 | 3/2005 | Ahmed et al. | |
| 6,867,389 B2 | 3/2005 | Shapovalov et al. | |
| 6,887,510 B2 | 5/2005 | Villareal | |
| 6,927,359 B2 | 8/2005 | Kleine et al. | |
| 7,083,642 B2 * | 8/2006 | Sirhan et al. | 623/1.42 |
| 7,135,039 B2 * | 11/2006 | De Scheerder et al. | 623/1.42 |
| 2001/0000802 A1 | 5/2001 | Soykan et al. | |
| 2001/0027291 A1 | 10/2001 | Shanley | |
| 2001/0027340 A1 | 10/2001 | Wright et al. | |
| 2001/0029351 A1 | 10/2001 | Falotico et al. | |
| 2001/0034363 A1 | 10/2001 | Li et al. | |
| 2001/0044648 A1 | 11/2001 | Wolinsky et al. | |
| 2001/0044652 A1 | 11/2001 | Moore | |
| 2002/0002400 A1 | 1/2002 | Drasler et al. | |
| 2002/0005206 A1 | 1/2002 | Falotico et al. | |
| 2002/0007209 A1 | 1/2002 | Scheerder et al. | |
| 2002/0010507 A1 | 1/2002 | Ehr et al. | |
| 2002/0013619 A1 | 1/2002 | Shanley | |
| 2002/0022876 A1 | 2/2002 | Richter et al. | |
| 2002/0028243 A1 | 3/2002 | Masters | |
| 2002/0032414 A1 | 3/2002 | Ragheb et al. | |
| 2002/0038145 A1 | 3/2002 | Jang | |
| 2002/0038146 A1 | 3/2002 | Harry | |
| 2002/0068969 A1 | 6/2002 | Shanley et al. | |
| 2002/0072511 A1 | 6/2002 | New et al. | |
| 2002/0082679 A1 | 6/2002 | Sirhan et al. | |
| 2002/0082680 A1 | 6/2002 | Shanley et al. | |
| 2002/0094985 A1 | 7/2002 | Herrmann et al. | |
| 2002/0107563 A1 | 8/2002 | Shanley | |
| 2002/0123801 A1 | 9/2002 | Pacetti et al. | |
| 2002/0142039 A1 | 10/2002 | Claude | |
| 2002/0155212 A1 | 10/2002 | Hossainy | |
| 2002/0165604 A1 | 11/2002 | Shanley | |
| 2003/0009214 A1 | 1/2003 | Shanley | |
| 2003/0028244 A1 | 2/2003 | Bates et al. | |
| 2003/0033007 A1 | 2/2003 | Sirhan et al. | |
| 2003/0036794 A1 | 2/2003 | Ragheb et al. | |
| 2003/0060877 A1 | 3/2003 | Falotico et al. | |
| 2003/0068355 A1 | 4/2003 | Shanley et al. | |
| 2003/0088307 A1 | 5/2003 | Shulze et al. | |
| 2003/0100865 A1 | 5/2003 | Santini, Jr. et al. | |
| 2003/0105511 A1 | 6/2003 | Welsh et al. | |
| 2003/0125803 A1 | 7/2003 | Vallana et al. | |
| 2003/0157241 A1 | 8/2003 | Hossainy et al. | |
| 2003/0167085 A1 | 9/2003 | Shanley | |
| 2003/0176915 A1 | 9/2003 | Wright et al. | |
| 2003/0199970 A1 | 10/2003 | Shanley | |
| 2003/0216699 A1 | 11/2003 | Falotico | |
| 2003/0225420 A1 | 12/2003 | Wardle | |
| 2004/0006382 A1 | 1/2004 | Sohier | |
| 2004/0024449 A1 | 2/2004 | Boyle | |
| 2004/0043510 A1 | 3/2004 | Shigetoh et al. | |
| 2004/0122505 A1 | 6/2004 | Shanley | |

(56) References Cited

U.S. PATENT DOCUMENTS

| | | |
|---|---|---|
| 2004/0127976 A1 | 7/2004 | Diaz |
| 2004/0127977 A1 | 7/2004 | Shanley |
| 2004/0142014 A1 | 7/2004 | Litvack et al. |
| 2004/0143321 A1 | 7/2004 | Litvack et al. |
| 2004/0143322 A1 | 7/2004 | Litvack et al. |
| 2004/0144506 A1 | 7/2004 | Walter et al. |
| 2004/0166140 A1 | 8/2004 | Santini, Jr. et al. |
| 2004/0193255 A1 | 9/2004 | Shanley et al. |
| 2004/0202692 A1 | 10/2004 | Shanley et al. |
| 2004/0204756 A1 | 10/2004 | Diaz et al. |
| 2004/0220660 A1 | 11/2004 | Shanley et al. |
| 2004/0220665 A1 | 11/2004 | Hossainy et al. |
| 2004/0225350 A1 | 11/2004 | Shanley et al. |
| 2004/0249449 A1 | 12/2004 | Shanley et al. |
| 2004/0254635 A1 | 12/2004 | Shanley et al. |
| 2005/0055078 A1 | 3/2005 | Campbell |
| 2005/0058684 A1 | 3/2005 | Shanley et al. |
| 2005/0060020 A1 | 3/2005 | Jenson |
| 2005/0061771 A1 | 3/2005 | Murphy |
| 2005/0064088 A1 | 3/2005 | Fredrickson |
| 2005/0074545 A1 | 4/2005 | Thomas |
| 2005/0075714 A1 | 4/2005 | Cheng et al. |
| 2005/0079199 A1 | 4/2005 | Heruth et al. |
| 2005/0100577 A1 | 5/2005 | Parker et al. |
| 2005/0106210 A1 | 5/2005 | Ding et al. |
| 2005/0113903 A1 | 5/2005 | Rosenthal et al. |
| 2005/0158360 A1 | 7/2005 | Falotico et al. |
| 2005/0160891 A1 | 7/2005 | Koch |
| 2005/0166389 A1 | 8/2005 | Perreault et al. |
| 2005/0222676 A1 | 10/2005 | Shanley et al. |
| 2005/0228490 A1 | 10/2005 | Hezi-Yamit et al. |
| 2005/0229670 A1 | 10/2005 | Perreault |
| 2005/0233062 A1 | 10/2005 | Hossainy et al. |
| 2005/0234538 A1 | 10/2005 | Litvack et al. |
| 2005/0234544 A1 | 10/2005 | Shanley |
| 2005/0238686 A1 | 10/2005 | Hossainy et al. |
| 2005/0240256 A1 | 10/2005 | Austin |
| 2005/0251248 A1 | 11/2005 | Chandresekara et al. |
| 2005/0273161 A1 | 12/2005 | Malik et al. |
| 2005/0278016 A1 | 12/2005 | Welsh et al. |
| 2006/0008503 A1 | 1/2006 | Shanley et al. |
| 2006/0009838 A1 | 1/2006 | Shanley et al. |
| 2006/0017834 A1 | 1/2006 | Konno et al. |
| 2006/0030931 A1 | 2/2006 | Shanley |
| 2006/0064157 A1 | 3/2006 | Shanley |
| 2006/0096660 A1 | 5/2006 | Diaz et al. |
| 2006/0122688 A1 | 6/2006 | Shanley et al. |
| 2006/0122697 A1 | 6/2006 | Shanley et al. |
| 2006/0177564 A1 | 8/2006 | Diaz et al. |
| 2006/0178734 A1 | 8/2006 | Parker et al. |
| 2006/0178735 A1 | 8/2006 | Litvack et al. |

FOREIGN PATENT DOCUMENTS

| | | |
|---|---|---|
| EP | 0335341 B1 | 3/1992 |
| EP | 0375520 B1 | 4/1993 |
| EP | 0567816 A1 | 4/1993 |
| EP | 0470246 B1 | 6/1995 |
| EP | 0470569 B1 | 11/1995 |
| EP | 0706376 B1 | 6/1997 |
| EP | 0540290 B1 | 1/1998 |
| EP | 0734698 B1 | 8/1998 |
| EP | 0627226 B1 | 12/1998 |
| EP | 0679373 B1 | 1/1999 |
| EP | 0566245 B1 | 6/1999 |
| EP | 0807424 B1 | 8/1999 |
| EP | 0734699 B1 | 4/2001 |
| EP | 1132058 A1 | 9/2001 |
| EP | 1172074 A2 | 1/2002 |
| EP | 0897700 B1 | 7/2002 |
| EP | 0747069 B1 | 9/2002 |
| EP | 0770401 B1 | 11/2002 |
| EP | 0950386 B1 | 4/2004 |
| EP | 1493456 A2 | 1/2005 |
| EP | 1498084 A2 | 1/2005 |
| EP | 0875218 B1 | 2/2005 |
| EP | 1181903 B1 | 2/2005 |
| EP | 0846447 B1 | 6/2005 |
| EP | 0956832 B1 | 6/2005 |
| EP | 0968013 B1 | 10/2005 |
| EP | 1236478 B1 | 10/2005 |
| EP | 1341479 B1 | 10/2005 |
| EP | 1600180 A2 | 11/2005 |
| EP | 1118325 B1 | 1/2006 |
| EP | 0853927 B1 | 5/2006 |
| EP | 1222941 B1 | 5/2006 |
| EP | 0973462 B1 | 6/2006 |
| EP | 1277449 B1 | 6/2006 |
| EP | 1561436 B1 | 8/2007 |
| EP | 1559439 B1 | 10/2007 |
| EP | 1518570 B1 | 1/2008 |
| EP | 1582180 B1 | 2/2008 |
| EP | 1223305 B1 | 4/2008 |
| EP | 1527754 B1 | 8/2008 |
| FR | 2764794 A1 | 12/1998 |
| WO | 90/13332 A1 | 11/1990 |
| WO | 91/10424 A1 | 7/1991 |
| WO | 91/11193 A1 | 8/1991 |
| WO | 91/12779 A1 | 9/1991 |
| WO | 92/12717 A2 | 8/1992 |
| WO | 92/15286 A1 | 9/1992 |
| WO | 93/06792 A1 | 4/1993 |
| WO | WO94/21308 A1 | 9/1994 |
| WO | WO94/24961 A1 | 11/1994 |
| WO | WO95/03036 A1 | 2/1995 |
| WO | WO95/03795 A1 | 2/1995 |
| WO | WO95/24908 A1 | 9/1995 |
| WO | WO96/03092 A1 | 2/1996 |
| WO | WO96/25176 A1 | 8/1996 |
| WO | WO96/29028 A1 | 9/1996 |
| WO | WO96/32907 A1 | 10/1996 |
| WO | WO97/04721 A1 | 2/1997 |
| WO | WO98/08566 A1 | 3/1998 |
| WO | WO98/18407 A1 | 5/1998 |
| WO | WO98/19628 A1 | 5/1998 |
| WO | WO98/23228 A1 | 6/1998 |
| WO | WO98/23244 A2 | 6/1998 |
| WO | WO98/33546 A1 | 8/1998 |
| WO | WO98/36784 A1 | 8/1998 |
| WO | WO98/58600 A1 | 12/1998 |
| WO | WO99/15108 A2 | 4/1999 |
| WO | WO99/16386 A1 | 4/1999 |
| WO | WO99/16477 A2 | 4/1999 |
| WO | WO99/23977 A1 | 5/1999 |
| WO | WO99/37245 A1 | 7/1999 |
| WO | WO99/44536 A1 | 9/1999 |
| WO | WO99/49928 A1 | 10/1999 |
| WO | WO99/55396 A1 | 11/1999 |
| WO | WO00/10613 A2 | 3/2000 |
| WO | WO00/10622 A1 | 3/2000 |
| WO | WO00/45744 A1 | 8/2000 |
| WO | WO00/69368 | 11/2000 |
| WO | WO00/71054 A1 | 11/2000 |
| WO | WO01/17577 A1 | 3/2001 |
| WO | WO01/45862 A1 | 6/2001 |
| WO | WO01/49338 A1 | 7/2001 |
| WO | WO01/87376 A1 | 11/2001 |
| WO | WO02/17880 A2 | 3/2002 |
| WO | WO02/26162 A2 | 4/2002 |
| WO | WO02/26281 A1 | 4/2002 |
| WO | WO02/32347 A2 | 4/2002 |
| WO | WO02/43788 A2 | 6/2002 |
| WO | WO02/060506 A1 | 8/2002 |
| WO | 02085253 | 10/2002 |
| WO | WO03/015664 A1 | 2/2003 |
| WO | WO2004/096093 A1 | 4/2003 |
| WO | WO03/048665 A1 | 6/2003 |
| WO | 03064383 | 8/2003 |
| WO | WO03/077730 A2 | 9/2003 |
| WO | WO2004/043510 A1 | 5/2004 |
| WO | WO2004/043511 A1 | 5/2004 |
| WO | WO2004/087015 A2 | 10/2004 |
| WO | WO2004/094096 A1 | 11/2004 |

(56) References Cited

FOREIGN PATENT DOCUMENTS

| WO | WO2004/096176 A2 | 11/2004 |
| --- | --- | --- |
| WO | WO2004/096311 A1 | 11/2004 |
| WO | WO2005/004945 A2 | 1/2005 |
| WO | WO2005/016187 A1 | 2/2005 |
| WO | WO2005/016396 A1 | 2/2005 |
| WO | WO2005/018606 A1 | 3/2005 |
| WO | WO2005/027794 A2 | 3/2005 |
| WO | WO2005/034805 A1 | 4/2005 |
| WO | WO2005/034806 A1 | 4/2005 |
| WO | WO2005/037444 A1 | 4/2005 |
| WO | WO2005/037447 A1 | 4/2005 |
| WO | WO2005/046521 A1 | 5/2005 |
| WO | WO2005/047572 A1 | 5/2005 |
| WO | WO2005/089951 A1 | 9/2005 |
| WO | WO2005/092420 A1 | 10/2005 |
| WO | WO2005/102590 A1 | 11/2005 |
| WO | WO2005/112570 A2 | 12/2005 |
| WO | WO2005/115277 A2 | 12/2005 |
| WO | WO2005/120397 A1 | 12/2005 |
| WO | WO2006/007473 A1 | 1/2006 |
| WO | WO2006/012034 A2 | 2/2006 |
| WO | WO2006/012060 A2 | 2/2006 |

OTHER PUBLICATIONS

Suzuki, Takeshi M.D. et al., "Stent-Based Delivery of Sirolimus Reduces Neointimal Formation in a Porcine Coronary Model," Circulation, Sep. 4, 2001, pp. 1188-1193.

Australian Examination Report mailed Jun. 4, 2009 from corresponding Australian Patent Application No. 2004247027.

Australian Examination Report mailed Oct. 26, 2010 from corresponding Australian Patent Application No. 2006223581.

Canadian Examination Report mailed Dec. 21, 2009 from corresponding Canadian Patent Application No. 2,499,594.

Supplementary European Search Report mailed Nov. 12, 2008 from corresponding European Patent Application No. 04753187.6.

European Official Communication mailed Nov. 18, 2009 from corresponding European Patent Application No. 04753187.6.

Japanese Preliminary Notice of Reasons for Rejection mailed Jul. 28, 2009 from corresponding Japanese Patent Application No. 2004-538450.

Japanese Preliminary Notice of Reasons for Rejection mailed Jan. 26, 2010 from corresponding Japanese Patent Application No. 2006-533368.

Japanese Notification of Reasons for Refusal mailed Apr. 26, 2011 from corresponding Japanese Patent Application No. 2008-501905.

Emanuelsson, Hakan, et al., "The Jostent Coronary Stent Range", Chapter 19, 3 pages.

Hwang, Chao-Wei, et al., "Physiological Transport Forces Govern Drug Distribution for Stent-Based Delivery", Circulation, Aug. 7, 2001, DD. 1-8,2001.

Serryus, Patrick W., et al., "The Effect of Variable Dose and Release Kinetics on Neointimal Hyperplasia using a Novel Paclitaxel-Eluting Stent Platform", Journal of the American COllege of Cardiology, vol. 46, No. 2, 2005, pp. 253-260.

West, Jennifer L., "Drug Delivery—Pulsed Polymers", Nature Materials, vol. 2, Nov. 2003, pp. 709-710.

European Office Action issued in the corresponding European patent application No. 11 008 893.7, dated Jun. 22, 2015.

\* cited by examiner

METHOD AND APPARATUS FOR LOADING A BENEFICIAL AGENT INTO AN EXPANDABLE MEDICAL DEVICE

CROSS-REFERENCE TO RELATED APPLICATIONS

This application is a divisional application of Ser. No. 12/841,903 filed May 13, 2007, which is a divisional application of Ser. No. 10/447,587 filed May 28, 2003, which claims priority to U.S. Provisional Patent Application Ser. No. 60/412,489, filed on Sep. 20, 2002, which is incorporated herein by reference in its entirety.

FIELD OF THE INVENTION

The invention relates to a method and apparatus for loading a beneficial agent, such as a drug into an expandable medical device, and more particularly, the invention relates to a method and apparatus for dispensing a beneficial agent into an expandable medical device such as a stent.

DESCRIPTION OF THE RELATED ART

Implantable medical devices are often used for delivery of a beneficial agent, such as a drug, to an organ or tissue in the body at a controlled delivery rate over an extended period of time. These devices may deliver agents to a wide variety of bodily systems to provide a wide variety of treatments.

One of the many implantable medical devices which have been used for local delivery of beneficial agents is the coronary stent. Coronary stents are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665; 4,739,762; and 4,776,337). Known construction materials for use in stents include polymers, organic fabrics and biocompatible metals, such as stainless steel, gold, silver, tantalum, titanium, and shape memory alloys, such as Nitinol.

Of the many problems that may be addressed through stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition, neointimal hyperplasia, and vascular smooth muscle cell proliferation, and which may ultimately result in renarrowing or even reocclusion of the lumen. Despite the introduction of improved surgical techniques, devices, and pharmaceutical agents, the overall restenosis rate is still reported in the range of 25% to 50% within six to twelve months after an angioplasty procedure. To treat this condition, additional revascularization procedures are frequently required, thereby increasing trauma and risk to the patient.

One of the techniques under development to address the problem of restenosis is the use of surface coatings of various beneficial agents on stents. U.S. Pat. No. 5,716,981, for example, discloses a stent that is surface-coated with a composition comprising a polymer carrier and paclitaxel (a well-known compound that is commonly used in the treatment of cancerous tumors). The patent offers detailed descriptions of methods for coating stem surfaces, such as spraying and dipping, as well as the desired character of the coating itself: it should "coat the stent smoothly and evenly" and "provide a uniform, predictable, prolonged release of the anti-angiogenic factor." Surface coatings, however, can provide little actual control over the release kinetics of beneficial agents. These coatings are necessarily very thin, typically 5 to 8 microns deep. The surface area of the stent, by comparison is very large, so that the entire volume of the beneficial agent has a very short diffusion path to discharge into the surrounding tissue.

Increasing the thickness of the surface coating has the beneficial effects of improving drug release kinetics including the ability to control drug release and to allow increased drug loading. However, the increased coating thickness results in increased overall thickness of the stent wall. This is undesirable for a number of reasons, including increased trauma to the vessel wall during implantation, reduced flow cross-section of the lumen after implantation, and increased vulnerability of the coating to mechanical failure or damage during expansion and implantation. Coating thickness is one of several factors that affect the release kinetics of the beneficial agent, and limitations on thickness thereby limit the range of release rates, duration of drug delivery, and the like that can be achieved.

In addition to sub-optimal release profiles, there are further problems with surface coated stents. The fixed matrix polymer carriers frequently used in the device coatings typically retain approximately 30% of the beneficial agent in the coating indefinitely. Since these beneficial agents are frequently highly cytotoxic, sub-acute and chronic problems such as chronic inflammation, late thrombosis, and late or incomplete healing of the vessel wall may occur. Additionally, the carrier polymers themselves are often highly inflammatory to the tissue of the vessel wall. On the other hand, use of biodegradable polymer carriers on stent surfaces can result in the creation of "virtual spaces" or voids between the stent and tissue of the vessel wall after the polymer carrier has degraded, which permits differential motion between the stent and adjacent tissue. Resulting problems include micro-abrasion and inflammation, stent drift, and failure to re-endothelialize the vessel wall.

Another significant problem is that expansion of the stent may stress the overlying polymeric coating causing the coating to plastically deform or even to rupture, which may therefore effect drug release kinetics or have other untoward effects. Further, expansion of such a coated stent in an atherosclerotic blood vessel will place circumferential shear forces on the polymeric coating, which may cause the coating to separate from the underlying stent surface. Such separation may again have untoward effects including embolization of coating fragments causing vascular obstruction.

In addition, it is not currently possible to deliver some drugs with a surface coating due to sensitivity of the drugs to water, other compounds, or conditions in the body which degrade the drugs. For example, some drugs lose substantially all their activity when exposed to water for a period of time. When the desired treatment time is substantially longer than the half life of the drug in water, the drug cannot be delivered by known coatings. Other drugs, such as protein or peptide based therapeutic agents, lose activity when exposed to enzymes, pH changes, or other environmental conditions.

These drugs which are sensitive to compounds or conditions in the body often cannot be delivered using surface coatings.

Accordingly, it would be desirable to provide an apparatus and method for loading a beneficial agent into an expandable medical device, such as a stent, for delivery of agents, such as drugs, to a patient.

SUMMARY OF THE INVENTION

The present invention relates to an apparatus and method for loading a beneficial agent in an expandable medical device.

In accordance with one aspect of the invention, a method for dispensing a beneficial agent into an expandable medical device includes the steps of placing an expandable medical device on a mandrel, the medical device forming a cylindrical device having a plurality of openings; and dispensing a beneficial agent into at least a portion of the plurality of openings.

In accordance with another aspect of the invention, a method for loading a beneficial agent in an expandable medical device includes the steps of dispensing a beneficial agent through a dispenser into a first opening in an expandable medical device; providing relative movement between the dispenser and the expandable medical device such that the dispenser is moved from alignment with the first opening in the expandable medical device to alignment with a second opening in the expandable medical device; and dispensing the beneficial agent into the second opening in the expandable medical device.

In accordance with a further aspect of the invention, an apparatus for loading a beneficial agent in an expandable medical device includes a mandrel; an expandable medical device having a plurality of openings, the expandable medical device mounted on the mandrel; and a dispenser configured to dispense a beneficial agent into the plurality of openings in the expandable medical device.

In accordance with a further aspect of the invention, a method for loading a stent with a beneficial agent includes the steps of providing a stent with a plurality of holes; and dispensing a beneficial agent through a piezo-electric micro-jet into the plurality of holes.

In accordance with an additional aspect of the invention, an apparatus for loading a beneficial agent in a medical device comprises a dispenser configured to dispense a beneficial agent into the plurality of openings in the medical device; an observation system configured to locate and identify the plurality of openings; and a central processing unit for controlling the dispensing of the beneficial agent into the openings of the medical device, wherein an amount and location of droplets of beneficial agent dispensed into each of the openings in the medical device is determined by the central processing unit based information obtained from the observation system.

In accordance with another aspect of the invention, a system for controlling a delivery of a beneficial agent into a plurality of openings of a medical device includes an observation system for mapping a medical device to obtain an actual position of a plurality of openings of the medical device; a central processing unit for comparing the actual position of the plurality of openings of the medical device to an anticipated position from a manufacturing specification; and a dispenser for dispensing a fluid beneficial agent into the plurality of openings.

In accordance with a further aspect of the invention, a system for controlling a delivery of a beneficial agent into an opening includes a mandrel having a plurality of expandable medical devices; a dispenser configured to dispense a first layer and a second layer of a beneficial agent into a plurality of openings in the expandable medical device; and a central processing unit for controlling the dispensing of the beneficial agent into the openings of the expandable medical device.

In accordance with another aspect of the invention, a method of removing stents from a mandrel includes the steps of radially expanding the stents by injecting air into at least a portion of the mandrel to inflate the mandrel and expand the stents; deflating the mandrel; and sliding the expanded stents off the mandrel.

BRIEF DESCRIPTION OF THE DRAWING FIGURES

The invention will now be described in greater detail with reference to the preferred embodiments illustrated in the accompanying drawings, in which like elements bear like reference numerals, and wherein.

DETAILED DESCRIPTION OF THE INVENTION

The present invention relates to a method and apparatus for loading a beneficial agent into an expandable medical device. More particularly, the invention relates to a method and apparatus for loading a beneficial agent in a stent.

First, the following terms, as used herein, shall have the following meanings:

The term "beneficial agent" as used herein is intended to have its broadest possible interpretation and is used to include any therapeutic agent or drug, as well as inactive agents such as barrier layers, carrier layers, therapeutic layers or protective layers.

The terms "drug" and "therapeutic agent" are used interchangeably to refer to any therapeutically active substance that is delivered to a bodily conduit of a living being to produce a desired, usually beneficial, effect. The present invention is particularly well suited for the delivery of antineoplastic, angiogenic factors, immuno-suppressants, anti-inflammatories and antiproliferatives (anti-restenosis agents) such as paclitaxel and Rapamycin for example, and anti-thrombins such as heparin, for example.

The term "matrix" or "biocompatible matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a therapeutic agent, a therapeutic agent, an activating agent or a deactivating agent, as defined herein. A matrix is also a medium that may simply provide support, structural integrity or structural barriers. The matrix may be polymeric, non-polymeric, hydrophobic, hydrophilic, lipophilic, amphiphilic, and the like.

The term "bioresorbable" refers to a matrix, as defined herein, that can be broken down by either chemical or physical process, upon interaction with a physiological environment. The bioresorbable matrix is broken into components that are metabolizable or excretable, over a period of time from minutes to years, preferably less than one year, while maintaining any requisite structural integrity in that same time period.

The term "polymer" refers to molecules formed from the chemical union of two or more repeating units, called monomers. Accordingly, included within the term "polymer" may be, for example, dimers, trimers and oligomers. The polymer may be synthetic, naturally-occurring or semisynthetic. In preferred form, the term "polymer" refers to molecules which typically have a $M_w$ greater than about 3000 and preferably greater than about 10,000 and a $M_w$ that is less than about 10 million, preferably less than about a million and more preferably less than about 200,000.

The term "openings" refers to holes of any shape and includes both through-openings and recesses.

Implantable Medical Devices with Holes

Figure 1:
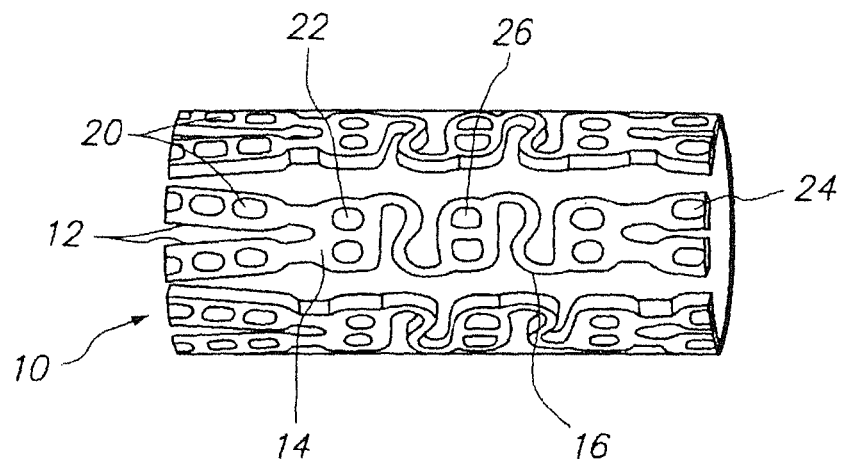
FIG. 1 is a perspective view of a therapeutic agent delivery device in the form of an expandable stent.

FIG. 1 illustrates a medical device 10 according to the present invention in the form of a stent design with large, non-deforming struts 12 and links 14, which can contain openings (or holes) 20 without compromising the mechanical properties of the struts or links, or the device as a whole. The non-deforming struts 12 and links 14 may be achieved by the use of ductile hinges which are described in detail in U.S. Pat. No. 6,241,762 which is incorporated hereby by reference in its entirety. The holes 20 serve as large, protected reservoirs for delivering various beneficial agents to the device implantation site.

As shown in FIG. 1, the openings 20 can be circular 22, rectangular 24, or D-shaped 26 in nature and form cylindrical, rectangular, or D-shaped holes extending through the width of the medical device 10. It can be appreciated that the openings 20 can be other shapes without departing from the present invention.

The volume of beneficial agent that can be delivered using openings 20 is about 3 to 10 times greater than the volume of a 5 micron coating covering a stent with the same stent/vessel wall coverage ratio. This much larger beneficial agent capacity provides several advantages. The larger capacity can be used to deliver multi-drug combinations, each with independent release profiles, for improved efficacy. Also, larger capacity can be used to provide larger quantities of less aggressive drugs and to achieve clinical efficacy without the undesirable side-effects of more potent drugs, such as retarded healing of the endothelial layer.

Figure 2:
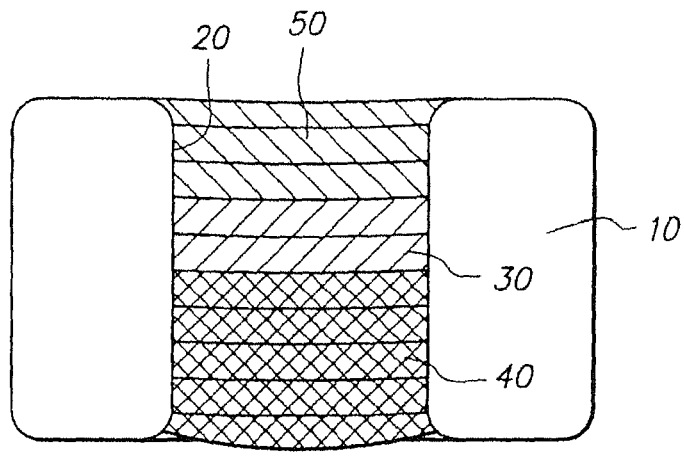
FIG. 2 is a cross-sectional view of a portion of a therapeutic agent delivery device having a beneficial agent contained in an opening in layers.

FIG. 2 shows a cross-section of a medical device 10 in which one or more beneficial agents have been loaded into the opening 20 in layers. Examples of some methods of creating such layers and arrangements of layers are described in U.S. patent application Ser. No. 09/948,989, filed on Sep. 7, 2001, which is incorporated herein by reference in its entirety. Although the layers are illustrated as discrete layers, the layers can also mix together upon delivery to result in an inlay of beneficial agent with concentration gradients of therapeutic agents but without distinct boundaries between layers.

According to one example, the total depth of the opening 20 is about 100 to about 140 microns, typically 125 microns and the typical layer thickness would be about 2 to about 50 microns, preferably about 12 microns. Each typical layer is thus individually about twice as thick as the typical coating applied to surface-coated stents. There would be at least two and preferably about ten to twelve such layers in a typical opening, with a total beneficial agent thickness about 25 to 28 times greater than a typical surface coating. According to one preferred embodiment of the present invention, each of the openings have an area of at least $5 \times 10^{-6}$ square inches, and preferably at least $7 \times 10^{-6}$ square inches. Typically, the openings are filled about 50% to about 75% full of beneficial agent.

Since each layer is created independently, individual chemical compositions and pharmacokinetic properties can be imparted to each layer. Numerous useful arrangements of such layers can be formed, some of which will be described below. Each of the layers may include one or more agents in the same or different proportions from layer to layer. The layers may be solid, porous, or filled with other drugs or excipients. As mentioned above, although the layers are deposited separately, they may mix forming an inlay without boundaries between layers.

As shown in FIG. 2, the opening 20 is filled with a beneficial agent. The beneficial agent includes a barrier layer 40, a therapeutic layer 30, and a cap layer 50.

Alternatively, different layers could be comprised of different therapeutic agents altogether, creating the ability to release different therapeutic agents at different points in time. The layers of beneficial agent provide the ability to tailor a delivery profile to different applications. This allows the medical device according to the present invention to be used for delivery of different beneficial agents to a wide variety of locations in the body.

A protective layer in the form of a cap layer 50 is provided at a tissue contacting surface of a medical device. The cap layer 50 can block or retard biodegradation of subsequent layers and/or blocks or retards diffusion of the beneficial agent in that direction for a period of time which allows the delivery of the medical device to a desired location in the body. When the medical device 10 is a stent which is implanted in a lumen, the barrier layer 40 is positioned on a side of the opening 20 facing the inside of the lumen. The barrier layer 40 prevents the therapeutic agent 30 from passing into the lumen and being carried away without being delivered to the lumen tissue.

Typical formulations for therapeutic agents incorporated in these medical devices are well known to those skilled in the art.

Uses for Implantable Medical Devices

Although the present invention has been described with reference to a medical device in the form of a stent, the medical devices of the present invention can also be medical devices of other shapes useful for site-specific and time-release delivery of drugs to the body and other organs and tissues. The drugs may be delivered to the vasculature including the coronary and peripheral vessels for a variety of therapies, and to other lumens in the body. The drugs may increase lumen diameter, create occlusions, or deliver the drug for other reasons.

Medical devices and stents, as described herein, are useful for the prevention of amelioration of restenosis, particularly after percutaneous transluminal coronary angioplasty and intraluminal stent placement. In addition to the timed or sustained release of anti-restenosis agents, other agents such as anti-inflammatory agents may be incorporated into the multi-layers incorporated in the plurality of holes within the device. This allows for site-specific treatment or prevention any complications routinely associated with stent placements that are known to occur at very specific times after the placement occurs.

Methods and Systems for Loading a Beneficial Agent in a Medical Device

Figure 3:
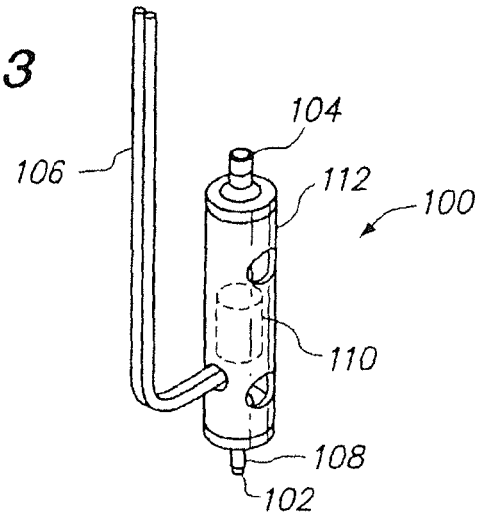
FIG. 3 is a cross-sectional view of a piezoelectric micro-jetting dispenser for delivery of a beneficial agent.

FIG. 3 shows a piezoelectric micro jetting dispenser 100 used to dispense a beneficial agent into the opening of a medical device. The dispenser 100 has a capillary tube 108 having a fluid outlet or orifice 102, a fluid inlet 104, and an electrical cable 106. The piezoelectric dispenser 100 preferably includes a piezo crystal 110 within a housing 112 for dispensing a fluid droplet through the orifice 102. The crystal 110 surrounds a portion of the capillary tube 108 and receives an electric charge that causes the crystal to vibrate. When the crystal vibrates inward, it forces a tiny amount of fluid out of the fluid outlet 102 of the tube 108 to fill an opening 20 in a medical device. In addition, when the crystal vibrates outward, the crystal pulls additional fluid into the tube 108 from a fluid reservoir connected to the inlet 104 to replace the fluid that has been dispensed into the opening of the medical device.

In one embodiment as shown in FIG. 3, the micro-jetting dispenser 100 includes an annular piezoelectric (PZT) actuator 110 bonded to a glass capillary 108. The glass capillary 108 is connected at one end to a fluid supply (not shown) and at the other end has an orifice 102 generally in the range of about 0.5 to about 150 microns, and more preferably about 30 to about 60 microns. When a voltage is applied to the PZT actuator, the cross-section of the capillary glass 108 is reduced/increased producing pressure variations of the fluid enclosed in the glass capillary 108. These pressure variations propagate in the glass capillary 108 toward the orifice 102. The sudden change in cross-section (acoustic impedance) at the orifice 102, causes a droplet to be formed. This mode of producing droplets is generally called drop on demand (DOD).

In operation, the micro jetting dispenser 100, depending on the viscosity and contact angle of the fluid, can require either positive or negative pressure at the fluid inlet 104. Typically, there are two ways to provide pressure at the fluid inlet 104. First, the pressure at the fluid inlet 104 can be provided by either a positive or a negative head by positioning of the fluid supply reservoir. For example, if the fluid reservoir is mounted only a few millimeters above the dispenser 100, a constant positive pressure will be provided. However, if the fluid reservoir is mounted a few millimeters below the dispenser 100, the orifice 102 will realize a negative pressure.

Alternatively, the pressure of the fluid at the inlet 104 can be regulated using existing compressed air or vacuum sources. For example, by inserting a pressure vacuum regulator between the fluid source and the dispenser 100, the pressure can be adjusted to provide a constant pressure flow to the dispenser 100.

In addition, a wide range of fluids including beneficial agents can be dispensed through the dispenser 100. The fluids preferably have a viscosity of no greater than about 40 centipoise. The droplet volume of the dispenser 100 is a function of the fluid, orifice 102 diameter, and actuator driving parameter (voltage and timing) and usually ranges from about 50 picoliters to about 200 picoliters per droplet. If a continuous droplet generation is desired, the fluid can be pressurized and a sinusoidal signal applied to the actuator to provide a continuous jetting of fluids. Depending on the beneficial agent dispensed, each droplet may appear more like a filament.

It can be appreciated that other fluid dispensing devices can be used without departing from the present invention. In one embodiment, the dispenser is a piezoelectric micro-jetting device manufactured by MicroFab Technologies, Inc., of Plano, Tex.

The electric cable 106 is preferably connected to associated drive electronics (not shown) for providing a pulsed electric signal. The electric cable 106 provides the electric signal to control the dispensing of the fluid through the dispenser 100 by causing the crystal to vibrate.

Figure 4:
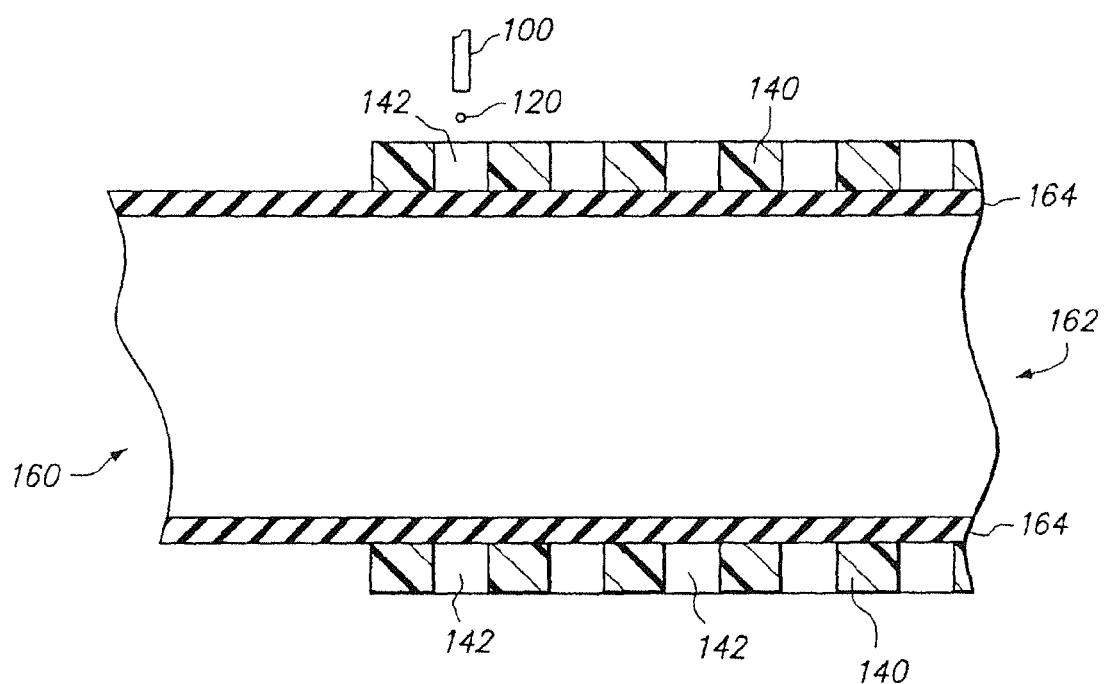
FIG. 4 is a cross-sectional view of a piezoelectric micro-jetting dispenser and an expandable medical device on a mandrel.

FIG. 4 shows an expandable medical device in the form of a stent 140 receiving a droplet 120 of a beneficial agent from a piezoelectric micro jetting dispenser 100. The stent 140 is preferably mounted to a mandrel 160. The stent 140 can be designed with large, non-deforming struts and links (as shown in FIG. 1), which contain a plurality of openings 142 without compromising the mechanical properties of the struts or links, or the device as a whole. The openings 142 serve as large, protected reservoirs for delivering various beneficial agents to the device implantation site. The openings 142 can be circular, rectangular, or D-shaped in nature and form cylindrical, rectangular or D-shaped holes extending through the width of the stent 140. In addition, openings 142 having a depth less than the thickness of the stent 140 may also be used. It can be appreciated that other shaped holes 142 can be used without departing from the present invention.

The volume of the hole 142 will vary depending on the shape and size of the hole 142. For example, a rectangular shaped opening 142 having a width of 0.1520 mm (0.006 inches) and a height of 0.1270 mm (0.005 inches) will have a volume of about 2.22 nanoliters. Meanwhile, a round opening having a radius of 0.0699 mm (0.00275 inches) will have a volume of about 1.87 nanoliters. A D-shaped opening having a width of 0.1520 mm (0.006 inches) along the straight portion of the D, has a volume of about 2.68 nanoliters. The openings according to one example are about 0.1346 mm (0.0053 inches) in depth having a slight conical shape due to laser cutting.

Although a tissue supporting device configuration has been illustrated in FIG. 1, which includes ductile hinges, it should be understood that the beneficial agent may be contained in openings in stents having a variety of designs including many of the known stents.

The mandrel 160 can include a wire member 162 encapsulated by an outer jacket 164 of a resilient or a rubber-like material. The wire member 162 may be formed from a metallic thread or wire having a circular cross-section. The metallic thread or wire is preferably selected from a group of metallic threads or wire, including Nitinol, stainless steel, tungsten, nickel, or other metals having similar characteristics and properties.

In one example, the wire member 162 has an outer diameter of between about 0.889 mm (0.035 inches) and about 0.991 mm (0.039 inches) for use with a cylindrical or implantable tubular device having an outer diameter of about 3 mm (0.118 inches) and an overall length of about 17 mm (0.669 inches). It can be appreciated that the outer diameter of the wire member 162 will vary depending on the size and shape of the expandable medical device 140.

Examples of rubber-like materials for the outer jacket 164 include silicone, polymeric materials, such as polyethylene, polypropylene, polyvinyl chloride (PVC), ethyl vinyl acetate (EVA), polyurethane, polyamides, polyethylene terephthalate (PET), and their mixtures and copolymers. However, it can be appreciated that other materials for the outer jacket 164 can be implemented, including those rubber-like materials known to those skilled in the art.

In one embodiment, the wire member 162 is encapsulated in a tubular outer jacket 164 having an inner diameter of about 0.635 mm (0.25 inches). The outer jacket 164 can be mounted over the wire member 162 by inflating the tubular member to increase to a size greater than the outer diameter of the wire member 162. The tubular member can be inflated using an air pressure device known to those skilled in the art. The wire member 162 is placed inside of the outer jacket 164 by floating the outer jacket 164 of silicon over the wire member 162. However, it can be appreciated that the wire member 162 can be encapsulated in an outer jacket of silicon or other rubber-like material by any method known to one skilled in the art.

In one embodiment for loading stents having a diameter of about 3 mm (0.118 inches) and a length of about 17 mm (0.669 inches), a wire member 162 having an outer diameter of 0.939 mm (0.037 inches) is selected. In one example, the wire member 162 is about 304.8 mm (12 inches) in length. The outer jacket 164 has an inner diameter of about 0.635 mm (0.025 inches).

The expandable medical device or stent 140 is then loaded onto the mandrel 160 in any method known to one skilled in the art. In one embodiment, the stents 140 and the mandrel 160 are dipped into a volume of lubricant to lubricate the stents 140 and the mandrel 160. The stents 140 are then loaded onto the mandrel 160. The drying of the stents 140 and the mandrel 160 create a substantially firm fit of the stents 140 onto the mandrel 160. Alternatively, or in addition to drying, the stents 140 can be crimped onto the mandrel by a method known to one skilled in the art onto the mandrel 160. The crimping ensures that the stents 140 will not move or rotate during mapping or filling of the openings.

Figure 5:
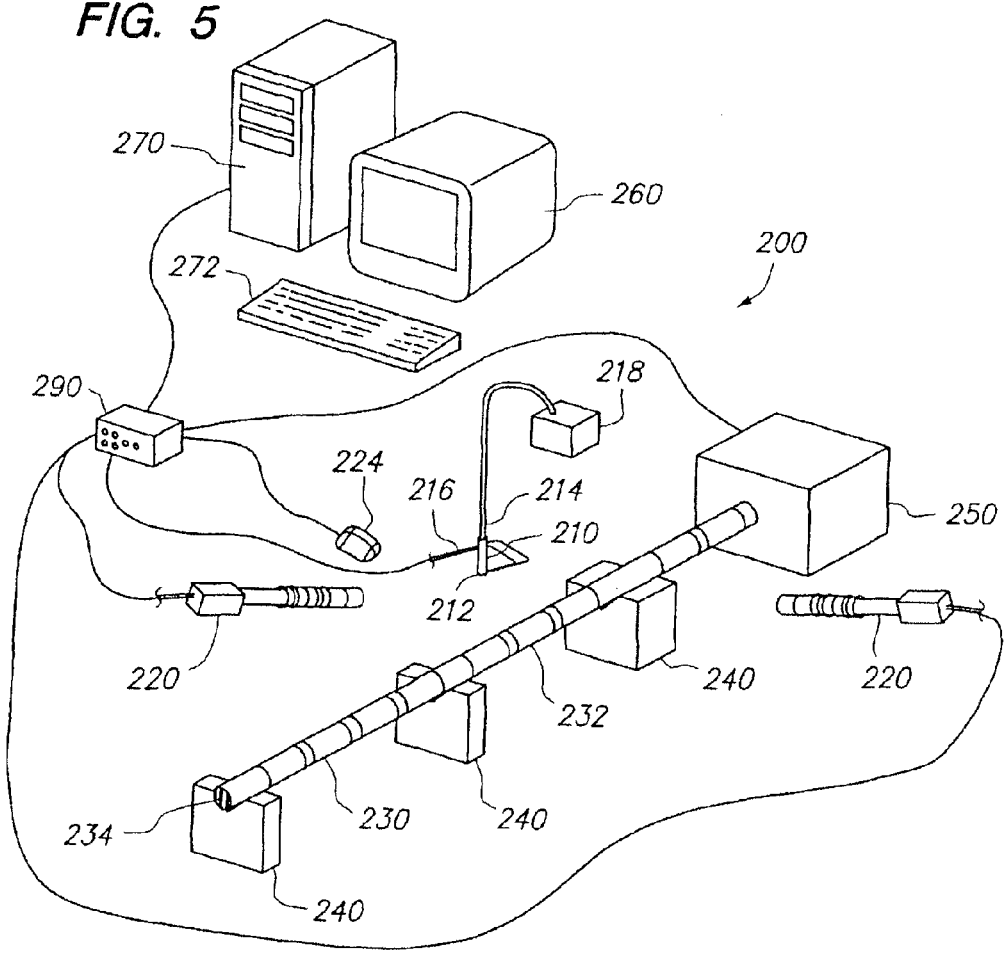
FIG. 5 is a perspective view of a system for loading an expandable medical device with a beneficial agent.

FIG. 5 shows a system 200 for loading a beneficial agent in an expandable medical device. The system 200 includes a dispenser 210 for dispensing a beneficial agent into an opening of an expandable medical device, a reservoir of beneficial agent 218 at least one observation system 220, and a mandrel 230 having a plurality of expandable medical devices 232 attached to the mandrel 230. The system 200 also includes a plurality of bearings 240 for supporting the rotating mandrel 230, a means for rotating and translating the mandrel 250 along a cylindrical axis of the expandable medical device 232, a monitor 260, and a central processing unit (CPU) 270.

The dispenser 210 is preferably a piezoelectric dispenser for dispensing a beneficial agent into the opening in the medical device 232. The dispenser 210 has a fluid outlet or orifice 212, a fluid inlet 214 and an electrical cable 216. The piezoelectric dispenser 200 dispenses a fluid droplet through the orifice 212.

At least one observation system 220 is used to observe the formation of the droplets and the positioning of the dispenser 210 relative to the plurality of openings in the medical device 232. The observation system 220 may include a charge coupled device (CCD) camera. In one embodiment, at least two CCD cameras are used for the filling process. The first camera can be located above the micro-jetting dispenser 210 and observes the filling of the medical device 232. The first camera is also used for mapping of the mandrel 230 as will be described below. A second camera is preferably located on a side of the micro-jetting dispenser 210 and observes the micro jetting dispenser 210 from a side or orthogonal view. The second camera is preferably used to visualize the micro-jetting dispenser during the positioning of the dispenser before loading of the medical device 232 with a beneficial agent. However, it can be appreciated that the observation system 220 can include any number of visualization systems including a camera, a microscope, a laser, machine vision system, or other known device to one skilled in the art. For example, refraction of a light beam can be used to count droplets from the dispenser. The total magnification to the monitor should be in the range of 50 to 100 times.

In one embodiment, a LED synchronized light 224 with the PZT pulse provides lighting for the system 200. The delay between the PZT pulse and the LED pulse is adjustable, allowing the capture of the droplet formation at different stages of development. The observation system 220 is also used in mapping of the mandrel 230 and medical devices 232 for loading of the openings. In one embodiment, rather than using a LED synchronized light 224, the lighting is performed using a diffused flourescent lighting system. It can be appreciated that other lighting systems can be used without departing from the present invention.

A plurality of expandable medical devices 232 are mounted to the mandrel 230 as described above. For example, a mandrel which is about 12 inches in length can accommodate about 11 stents having a length of about 17 mm each. Each mandrel 230 is labeled with a bar code 234 to ensure that each mandrel is properly identified, mapped, and then filled to the desired specifications.

Figure 6:
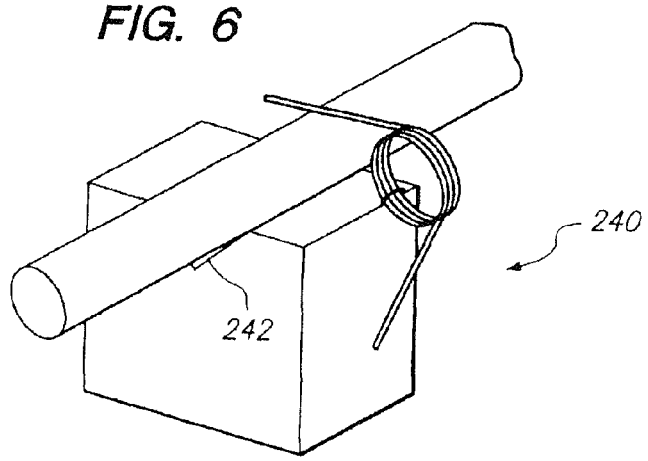
FIG. 6 is a perspective view of a bearing for use with the system of FIG. 5.

The mandrel 230 is positioned on a plurality of bearings 240. As shown in FIG. 6, one example of the bearings 240 have a V-shaped notch 242. The mandrel 230 is positioned within the V-shaped notch 242 and secured using a clip 244. The clip 244 is preferably a coil spring, however, other means of securing the mandrel within the V-shaped notch can be used including any type of clip or securing means can be used. The bearings 240 can be constructed of a metallic material, preferably different than the mandrel wire, such as stainless steel, copper, brass, or iron.

The mandrel 230 is connected to a means for rotating and translating the mandrel 250 along the cylindrical axis of the medical device 232. The means for rotating and translating the mandrel 250 can be any type or combination of motors or other systems known to one skilled in the art.

In one embodiment, the mandrel 250 and medical device 232 are moved from a first position to a second position to fill the openings of the medical device 232 with the beneficial agent. In an alternative embodiment, the system further includes a means for moving the dispensing system along the cylindrical axis of the medical device 232 from a first position to a second position.

A monitor 260 is preferably used to observe the loading of the medical device 232 with a beneficial agent. It can be appreciated that any type of monitor or other means of observing the mapping and loading process can be used.

A central processing unit 270 (or CPU) controls the loading of the medical device 232 with the beneficial agent. The CPU 270 provides processing of information on the medical device 232 for the dispensing of the beneficial agent. The CPU 270 is initially programmed with the manufacturing specifications as to the size, shape and arrangement of the openings in the medical device 232. A keyboard 272 is preferably used to assist with the loading of the CPU 270 and for input of information relating to the loading process.

The medical devices 232 are preferably affixed to the mandrel 230 and mapped prior to the loading process. The mapping process allows the observation system and associated control system to determine a precise location of each of the openings which may vary slightly from device to device and mandrel to mandrel due to inaccuracies of loading the devices on the mandrels. This precise location of each of the openings is then saved as the specific map for that specific mandrel. The mapping of the mandrel 230 is performed by using the observation system to ascertain the size, shape and arrangement of the openings of each medical device 232 located on the mandrel 230. Once the mandrel 230 including the plurality of medical devices 232 have been mapped, the mapping results are compared to the manufacturing specifications to provide adjustments for the dispenser to correctly dispense the beneficial agent into each of the holes of the medical device 232.

In an alternative embodiment, the mapping of the mandrel 230 is performed on an opening by opening comparison. In operation, the observation system maps a first opening in the medical device and compares the mapping result to the manufacturing specifications. If the first opening is positioned as specified by the manufacturing specifications, no adjustment is needed. However, if the first opening is not positioned as specified by the manufacturing specifications, an adjustment is recorded and an adjustment is made during the dispensing process to correct for the position which is different than as specified in the manufacturing specifications. The mapping is repeated for each opening of the medical device until each medical device 232 has been mapped. In addition, in one embodiment, if an opening is mapped and the opening is positioned pursuant to the manufacturing specifications, the mapping process can be designed to proceed to map at every other opening or to skip any number of openings without departing from the present invention.

After the mandrel has been mapped, the medical device 232 is filled with the beneficial agent based on the manufacturers' specification and adjustments from the mapping results. The CPU provides the programmed data for filling of each medical device 232. The programmed data includes the medical device design code, date created, lot number being created, number of medical devices 232 on the mandrel, volume of each opening in the medical device 232, different beneficial agents to be loaded or dispensed into the openings in the medical device 232, the number of layers, drying/baking time for each layer, and any other data.

In one embodiment, the medical device 232 will have at least 10 beneficial agent layers which will be filled including at least one barrier layer, at least one therapeutic layer having a beneficial agent, and at least one cap layer. The beneficial agent layers may include layers which vary in concentration and strength of each solution of drug or therapeutic agent, amount of polymer, and amount of solvent.

In operation, the operator will input or scan the bar code 234 of the mandrel into the CPU 270 before the filling process begins. The initial filling generally includes a mixture of polymer and solvent to create a barrier layer. Each of the openings are typically filled to about 80% capacity and then the mandrel is removed from the system and placed into an oven for baking. The baking process evaporates the liquid portion or solvent from the openings leaving a solid layer. The mandrel is typically baked for about 60 minutes plus or minus 5 minutes at about 55 degrees C. To assist in error prevention, the CPU software receives the bar code of the mandrel and will not begin filling the second layer until at least 60 minutes since the last filling. The second layer and subsequent layers are then filled in the same manner as the first layer until the opening has been filled to the desired capacity. The reservoir 218 can also be bar coded to identify the solution in the reservoir.

The observation system 220 also can verify that the dispenser 210 is dispensing the beneficial agent into the openings through either human observation on the monitor 270 or via data received from the observation system and conveyed to the CPU to confirm the dispensing of the beneficial agent in the openings of the medical device 232. Alternatively, refraction of a light beam can be used to count droplets dispensed at a high speed.

The dispensers 100 run very consistently for hours at a time, but will drift from day to day. Also, any small change in the waveform will change the drop size. Therefore, the output of the dispenser 100 can be calibrated by firing a known quantity of drops into a cup and then measuring the amount of drug in the cup. Alternatively, the dispenser 100 can be fired into a cup of known volume and the number of drops required to exactly fill it can be counted.

In filling the openings of the medical device 232, the micro-jetting dispenser 100 dispenses a plurality of droplets into the opening. In one preferred embodiment, the dispenser is capable of dispensing 3000 shots per second through a micro-jetting dispenser of about 40 microns. However, the droplets are preferably dispensed at between about 8 to 20 shots per hole depending on the amount of fill required. The micro-jetting dispenser fills each hole (or the holes desired) by proceeding along the horizontal axis of the medical device 232. The CPU 270 turns the dispenser 100 on and off to fill the openings substantially without dispensing liquid between openings on the medical device. Once the dispenser has reached an end of the medical device 232, the means for rotating the mandrel rotates the mandrel and a second passing of the medical device 232 along the horizontal axis is performed. In one embodiment, the medical devices 232 are stents having a diameter of about 3 mm and a length of about 17 mm and can be filled in about six passes. Once the medical device 232 is filled, the dispenser 210 moves to the next medical device 232 which is filled in the same manner.

The CPU 270 insures that the mandrel is filled accurately by having safety factors built into the filling process. It has also been shown that by filling the openings utilizing a micro-jetting dispenser, the amount of drugs or therapeutic agent used is substantially less than coating the medical device 232 using previously known method including spraying or dipping. In addition, the micro-jetting of a beneficial agent provides an improved work environment by exposing the worker to a substantially smaller quantity of drugs than by other known methods.

The system 200 also includes an electrical power source 290 which provides electricity to the piezoelectric micro-jetting dispenser 210.

The medical devices 232 can be removed from the mandrel by expanding the devices and sliding them off the mandrel. In one example, stents can be removed from the mandrel by injecting a volume of air between the outer diameter of the wire member 162 and the inner diameter of the outer jacket. The air pressure causes the medical device 232 to expand such that the inner diameter of the medical device 232 is greater than the outer diameter of the mandrel. In one embodiment, a die is place around the mandrel to limit the expansion of the medical device 232 as the air pressure between the outer diameter of the wire member 162 and the inner diameter of the outer jacket 164. The die can be constructed of stainless steel or plastics such that the medical devices 232 are not damaged during removal from the mandrel. In addition, in a preferred embodiment, the medical devices 232 are removed four at a time from the mandrel. A 12-inch mandrel will accommodate about 11, 3 mm by 17 mm medical devices having approximately 597 openings.

Example 1

In the example below, the following abbreviations have the following meanings. If an abbreviation is not defined, it has its generally accepted meaning.

DMSO=Dimethyl Sulfoxide

IV=Inherent Viscosity

PLGA=poly(lactide-co-glycolide)

TABLE I

| Solutions | Drug | Polymer | Solvent |
| --- | --- | --- | --- |
| A | None | 4% PLGA 50/50 IV = 0.82 | DMSO |
| DA | 0.64% paclitaxel | 8% PLGA 50/50 IV = 0.59 | DMSO |
| DA | 0.64% paclitaxel | 8% PLGA 50/50 IV = 0.60 | DMSO |
| DD | 0.14% paclitaxel | 8% PLGA 50/50 IV = 0.59 | DMSO |
| L | None | 8% PLGA 50/50 IV = 0.59 | DMSO |

TABLE II

| Layer No. | Solution | Layer No., this Solution |
| --- | --- | --- |
| 1 | A | 1 |
| 2 | A | 2 |
| 3 | A | 3 |
| 4 | A | 4 |
| 5 | A | 5 |
| 6 | A | 6 |
| 7 | A | 7 |
| 8 | A | 8 |
| 9 | A | 9 |
| 10 | DA | 1 |
| 11 | DA | 2 |
| 12 | DD | 1 |
| 13 | L | 1 |

A plurality of medical devices, preferably 11 medical devices per mandrel are placed onto a series of mandrels. Each mandrel is bar coded with a unique indicia which identifies at least the type of medical device, the layers of beneficial agents to be loaded into the opening of the medical devices, and a specific identity for each mandrel. The bar code information and the mapping results are stored in the CPU for loading of the stent.

A first mixture of poly(latide-co-glycolide) (PLGA) (Birmingham Polymers, Inc.), and a suitable solvent, such as DMSO is prepared. The mixture is loaded by droplets into holes in the stent. The stent is then preferably baked at a temperature of 55 degrees C. for about 60 minutes to evaporate the solvent to form a barrier layer. A second layer is laid over the first by the same method of filling polymer solution into the opening followed by solvent evaporation. The process is continued until 9 individual layers have been loaded into the openings of the medical device to form the barrier layer.

A second mixture of paclitaxel, PLGA, and a suitable solvent such as DMSO forming a therapeutic layer is then introduced into the openings of the medical device over the barrier layer. The solvent is evaporated to form a drug filled protective layer and the filling and evaporation procedure repeated until the hole is filled until the desired amount of paclitaxel has been added to the openings of the medical device.

A third mixture of PLGA and DMSO is then introduced into the openings over the therapeutic agent to form a cap layer. The solvent is evaporated and the filling and evaporation procedure repeated until the cap layer has been added to the medical device, in this embodiment, a single cap layer has been added.

In order to provide a plurality of layers of beneficial agents having a desired solution, the reservoir is replaced and the piezoelectric micro jetting dispenser is cleaned. The replacement of the reservoir and cleaning of the dispenser insures that the different beneficial layers have a desired solution including the correct amount of drugs, solvent, and polymer.

Following implantation of the filled medical device in viva, the PLGA polymer degrades via hydrolysis and the paclitaxel is released.

While the invention has been described in detail with reference to the preferred embodiments thereof, it will be apparent to one skirled in the art that various changes and modifications can be made and equivalents employed, without departing from the present invention.

What is claimed is:

1. A method for loading a beneficial agent into a medical device, the method comprising:
    mounting the medical device over a mandrel, the medical device including a plurality of through-holes extending through a thickness of a wall of the medical device from a first side to a second side, the mandrel having an resilient outer jacket;
    sealing one of the plurality of through-holes at the first side of the respective through-hole with the resilient outer jacket of the mandrel to substantially prevent a beneficial agent from leaking at an interface of the resilient outer jacket and the medical device to prevent the beneficial agent from passing to the first side of the respective through-hole;
    at least partially filling the respective through-hole with the beneficial agent delivered from an automated microjetting dispenser;
    substantially solidifying the beneficial agent; and
    removing the resilient outer jacket of the mandrel from the respective through-hole.

2. The method of claim 1, wherein the resilient outer jacket of the mandrel is formed of a rubber-like material.

3. The method of claim 2, wherein the resilient outer jacket of the mandrel is formed of the rubber-like material, and the medical device is a stent.

4. The method of claim 1, wherein the plurality of through-holes are formed by lasercutting.

5. The method of claim 1, wherein the medical device is a metallic medical device.

6. The method of claim 1, wherein the respective through-hole has an area of at least $5 \times 10^{-6}$ square inches.

7. The method of claim 1, wherein the beneficial agent includes a drug and a polymer matrix.

8. The method of claim 1, wherein the step of substantially solidifying includes drying the beneficial agent.

9. The method of claim 1, wherein the micro jetting dispenser is a piezoelectric micro jetting dispenser.

* * * * *